(12) United States Patent
Eckhardt et al.

(10) Patent No.: US 8,426,213 B2
(45) Date of Patent: Apr. 23, 2013

(54) HYDROGEN PEROXIDE DROPLET-BASED ASSAYS

(75) Inventors: Allen E. Eckhardt, Durham, NC (US); Vijay Srinivasan, Durham, NC (US); Vamsee K. Pamula, Durham, NC (US)

(73) Assignee: Advanced Liquid Logic Inc, Research Triangle Park, NC (US)

( * ) Notice: Subject to any disclaimer, the term of this patent is extended or adjusted under 35 U.S.C. 154(b) by 0 days.

(21) Appl. No.: 12/529,052

(22) PCT Filed: Mar. 5, 2008

(86) PCT No.: PCT/US2008/055891
§ 371 (c)(1),
(2), (4) Date: Aug. 28, 2009

(87) PCT Pub. No.: WO2008/109664
PCT Pub. Date: Sep. 12, 2008

(65) Prior Publication Data
US 2010/0028920 A1    Feb. 4, 2010

Related U.S. Application Data

(60) Provisional application No. 60/892,971, filed on Mar. 5, 2007, provisional application No. 60/980,186, filed on Oct. 16, 2007.

(51) Int. Cl.
*G01N 33/50* (2006.01)

(52) U.S. Cl.
USPC ............. 436/135; 435/4; 435/14; 435/25; 435/26; 435/27; 435/28; 436/53; 436/91; 436/92; 436/93; 436/94; 436/95; 436/96; 436/97; 436/98; 436/99; 436/164; 436/166; 436/172

(58) Field of Classification Search .......... 435/4, 14, 435/25–28; 436/53, 91–99, 164, 166, 172, 436/135
See application file for complete search history.

(56) References Cited

U.S. PATENT DOCUMENTS

| 3,630,957 | A | * | 12/1971 | Rey et al. ............... 436/66 |
| 4,247,297 | A | * | 1/1981 | Berti et al. ............. 436/169 |
| 4,251,629 | A | * | 2/1981 | Yamanisi et al. ....... 435/28 |
| 4,260,392 | A | * | 4/1981 | Lee ........................ 435/22 |
| 4,260,679 | A | * | 4/1981 | Tsuda et al. ............ 435/10 |

(Continued)

FOREIGN PATENT DOCUMENTS
WO    WO2006081558 A1    8/2006

OTHER PUBLICATIONS
Zaitsu, K. et al, Analytical Biochemistry 1980, 109, 109-113.*

(Continued)

*Primary Examiner* — Arlen Soderquist
(74) *Attorney, Agent, or Firm* — Ward & Smith, P.A.; William A. Barrett

(57) ABSTRACT

The present invention relates to providing improved hydrogen peroxide assays, as well as droplet actuators for conducting such assays. The droplet actuators of the invention may be used to conduct droplet-based hydrogen peroxide assays. They may also be associated with detectors for analyzing the results of the hydrogen peroxide assays of the invention. They may be provided as components of systems which control droplet operations and/or detection for conducting the hydrogen peroxide assays. Measurement by the detector may be used to quantify the presence of an analyte in a sample.

32 Claims, 3 Drawing Sheets

U.S. PATENT DOCUMENTS

| | | | | |
|---|---|---|---|---|
| 4,269,938 | A * | 5/1981 | Frank | 435/7.9 |
| 4,336,330 | A * | 6/1982 | Bauer | 435/14 |
| 4,353,983 | A * | 10/1982 | Siddiqi | 205/777.5 |
| 4,397,956 | A * | 8/1983 | Maggio | 436/34 |
| 4,605,615 | A * | 8/1986 | Ishikawa et al. | 435/16 |
| 4,649,121 | A * | 3/1987 | Ismail et al. | 436/14 |
| 4,659,677 | A * | 4/1987 | Glover et al. | 436/174 |
| 4,778,893 | A * | 10/1988 | Buckler et al. | 546/155 |
| 4,781,890 | A * | 11/1988 | Arai et al. | 422/428 |
| 4,894,472 | A * | 1/1990 | Seng et al. | 558/405 |
| 4,895,799 | A * | 1/1990 | Kruse-Muller et al. | 435/18 |
| 4,988,616 | A * | 1/1991 | Heidenreich et al. | 435/4 |
| 5,084,381 | A | 1/1992 | Akimoto et al. | |
| 5,110,724 | A * | 5/1992 | Hewett | 435/11 |
| 5,334,508 | A * | 8/1994 | Hoenes | 435/25 |
| 5,453,360 | A * | 9/1995 | Yu | 435/28 |
| 5,603,351 | A * | 2/1997 | Cherukuri et al. | 506/33 |
| 5,879,632 | A * | 3/1999 | Demers | 422/100 |
| 6,162,397 | A * | 12/2000 | Jurik et al. | 422/423 |
| 6,251,083 | B1 * | 6/2001 | Yum et al. | 600/584 |
| 6,294,063 | B1 | 9/2001 | Becker et al. | |
| 6,565,727 | B1 * | 5/2003 | Shenderov | 204/600 |
| 2002/0058332 | A1 * | 5/2002 | Quake et al. | 435/288.3 |
| 2002/0063060 | A1 * | 5/2002 | Gascoyne et al. | 204/471 |
| 2003/0121788 | A1 * | 7/2003 | Gascoyne et al. | 204/547 |
| 2003/0173223 | A1 * | 9/2003 | Gascoyne et al. | 204/547 |
| 2004/0058450 | A1 * | 3/2004 | Pamula et al. | 436/150 |
| 2005/0038329 | A1 * | 2/2005 | Morris et al. | 600/319 |
| 2005/0106742 | A1 | 5/2005 | Wahl | |
| 2005/0272159 | A1 * | 12/2005 | Ismagilov et al. | 436/34 |
| 2006/0114296 | A1 * | 6/2006 | Gascoyne et al. | 347/73 |
| 2006/0254933 | A1 | 11/2006 | Adachi et al. | |

OTHER PUBLICATIONS

Fowler, J. et al, Proceedings of the IEEE Conference on MEMS, Las Vegas, NV, Jan. 2002, 97-100.*

Taniguchi, T. et al, Lab on a Chip 2002, 2, 19-23.*

Richter, T. et al, Sensors and Actuators B 2002, 81, 369-376.*

Schwartz, J. A. et al, Lab on a Chip 2004, 4, 11-17.*

Gascoyne, P. R. C. et al, Lab on a Chip 2004, 4, 299-309.*

Satoh, W. et al, Analytical Chemistry 2005, 77, 6857-6863.*

Schilstra, M. J. et al, Biochemistry 1993, 32, 7686-7691.*

Sanz, V. et al, Journal of the American Chemical Socoety 2005, 127, 1038-1048.*

Martinello, F. et al, Chinica Chimica Acta 2006, 373, 108-116.*

Jie Ding, "System level architectural optimization of semi-reconfigurable microfluidic system," M.S. Thesis, Duke University Dept of Electrical Engineering, 2000.

Pollack et al., "Electrowetting-Based Actuation of Droplets for Integrated Microfluidics," Lab on a Chip (LOC), vol. 2, pp. 96-101, 2002.

Vijay Srinivasan, Vamsee K. Pamula, Richard B. Fair, "An integrated digital microfluidic lab-on-a-chip for clinical diagnostics on human physiological fluids," Lab on a Chip (LOC), vol. 4, pp. 310-315, 2004.

Vijay Srinivasan, Vamsee K. Pamula, Richard B. Fair, "Droplet-based microfluidic lab-on-a-chip for glucose detection," Analytica Chimica Acta, vol. 507, No. 1, pp. 145-150, 2004.

Srinivasan, et al., "Integrated chemical/biochemical sample collection, pre-concentration, and analysis on a digital microfluidic lab-on-a-chip platform," Lab-on-a-Chip: Platforms, Devices, and Applications, Conf. 5591, SPIE Optics East, Philadelphia, Oct. 25-28, 2004.

Fair, et al., "Integrated chemical/biochemical sample collection, pre-concentration, and analysis on a digital microfluidic lab-on-a-chip platform," Lab-on-a-Chip: Platforms, Devices, and Applications, Conf. 5591, SPIE Optics East, Philadelphia, Oct. 25-28, 2004.

Terry, S.C., J.H. Jerman, and J.B. Angell, "A Gas Chromatographic Air Analyzer Fabricated on a Silicon Wafer," IEEE Transactions on Electron Devices, vol. ED-26, 1979, pp. 1880-1886.

Tuckerman, D.B. and R.F.W. Pease, "High-Performance Heat Sinking for VLSI," IEEE Electron Device Letters, 1981, pp. 126-129.

Batchelder, J.S., "Dielectrophoretic manipulator," Review of Scientific Instruments, vol. 54, 1983, pp. 300-302.

Manz, A., N. Graber, and H.M. Widmer, "Miniaturized Total Chemical Analysis Systems: a Novel Concept for Chemical Sensing," Sensors and Actuators B: Chemical, 1990, pp. 244-248.

Welters, W.J.J. and L.G.J. Fokkink, "Fast Electrically Switchable Capillary Effects," Langmuir, vol. 14, Mar. 1998, pp. 1535-1538.

McDonald, J.C., D.C. Duffy, J.R. Anderson, D.T. Chiu, H. Wu, O.J.A. Schuueller, and G.M. Whitesides, "Fabrication of Microfluidic systems in poly (dimethylsiloxane)," Electrophoresis, vol. 21, 2000, pp. 27-40.

A. Wego, S. Richter, L. Pagel, "Fluidic microsystems based on printed circuit board technology," Journal of Micromechanics and Microengineering, vol. 11, No. 5, pp. 528-531 (Sep. 2001).

Moon H, Cho SK, Garrell RL, et al., "Low voltage electrowetting-on-dielectric," Journal of Applied Physics, vol. 92 (7): pp. 4080-4087, Oct. 1, 2002.

Becker, H., et al. "Polymer microfluidic devices," Talanta, vol. 56, Feb. 2002, pp. 267-287.

Youn, J.-Y. et al., "Preventing Biomolecular Adsorption in Electrowetting-Based Biofluidic Chips," Analytical Chemistry, vol. 75, Oct. 2003, pp. 5097-5102.

P.Y. Chiou, H. Moon, H. Toshiyoshi, C.-J. Kim, and M.C. Wu, "Light actuation of liquid by optoelectrowetting," Sensors and Actuators A: Physical, vol. 104, May 2003, pp. 222-228.

Squires, T.M. and S.R. Quake, "Microfluidics: Fluid physics at the nanoliter scale," Reviews of Modern Physics, vol. 77, Oct. 2005, pp. 977-1026.

Fouillet, Y., D. Jary, A.G. Brachet, C. Chabrol, J. Boutet, P. Clementz, R. Charles, and C. Peponnet, "Design and Validation of a Complex Generic Fluidic Microprocessor Based on EWOD Droplet for Biological Applications," 9th International Conference on Miniaturized Systems for Chemistry and Life Sciences (MicroTAS), Boston, MA: 2005, pp. 58-60.

Z. Guttenberg, H. Muller, H. Habermuller, A. Geisbauer, J. Pipper, J. Felbel, M. Kielpinski, J. Scriba, and A. Wixforth, "Planar chip devices for PCR and hybridization with surface acoustic wave pump.," Lab on a chip, vol. 5, Mar. 2005, pp. 12617-12622.

Yager, P., T. Edwards, E. Fu, K. Helton, K. Nelson, M.R. Tam, and B.H. Weigl, "Microfluidic diagnostic technologies for global public health," Nature, vol. 442, 2006, pp. 412-418.

Cooney, C.G., C-Y. Chen, M.R. Emerling, A Nadim, and J.D. Sterling, Microfluidics and Nanofluidics, vol. 2 Mar. 2006, pp. 435-446.

Chatterjee, D., B. Hetayothin, A.R. Wheeler, D.J. King, and R.L. Garrell, "Droplet-based microfluidics with nonaqueous solvents and solutions.," Lab on a Chip, vol. 6, Feb. 2006, pp. 199-206.

M.Madou, J. Zoval, G. Jia, H. Kido, J. Kim, "Lab on a CD," Annual Review of Biomedical Engineering, vol. 8, pp. 601-628, 2006.

Yi, U.-C. and C.-J. Kim, "Characterization of electrowetting actuation on addressable single-side coplanar electrodes," Journal of Micromechanics and Microengineering, vol. 16, Oct. 2006, pp. 2053-2059.

Dubois, P., G. Marchand, Y. Fouillet, J. Berthier, T. Douki, F. Hassine, S. Gmouh, and M. Vaultier, "Ionic Liquid Droplet as e-Microreactor," Analytical Chemistry, vol. 78, 2006, pp. 4909-4917.

Whitesides, G.M., "The origins and the future of Microfluidics," Nature, vol. 442, 2006, pp. 368-373.

Chin, C.D., V. Linder, and S.K. Sia, "Lab-on-a-chip devices for global health: past studies and future opportunities.," Lab on a Chip, vol. 7, Jan. 2007, pp. 41-57.

Baviere, R., J. Boutet, and Y. Fouillet, "Dynamics of droplet transport induced by electrowetting actuation," Microfluidics and Nanofluidics, vol. 4, May 2007, pp. 287-294.

Paik, P.Y., V.K. Pamula, and K. Chakrabarty, "A Digital-Microfluidic Approach to Chip Cooling," IEEE Design & Test of Computers, vol. 25, Jul. 2008, pp. 372-381.

Teh, S.-Y., R. Lin, L.-H. Hung, and A.P. Lee, "Droplet microfluidics.," Lab on a chip, vol. 8 Feb. 2008, pp. 198-220.

Huebner, A., S. Sharma, M. Srisa-Art, F. Hollfelder, J.B. Edel, and A.J. DeMello, "Microdroplets: a sea of applications?," Lab on a Chip, vol. 8, Aug. 2008, pp. 1244-1254.

Gong, J. and C.-J.C. Kim, "Direct-referencing two-dimensional-array digital microfluidics using multi-layer printed circuit board," Journal of Microelectromechanical Systems, vol. 17, Jan. 2008, pp. 257-264.

Miller, E.M. and A.R. Wheeler, "A Digital Microfluidic Approach to Homogeneous Enzyme Assays," Analytical Chemistry, vol. 80, 2008, pp. 1614-1619.

Luk, V.N., Pluronic additives: a solution to sticky problems in digital microfluidics.,: Langmuir: the ACS journal of surfaces ans colloids, vol. 24, Jun. 2008, pp. 6382-6389.

L. Luan, R.D. Evans, N.M. Jokerst, and R.B. Fair, "Integrated Optical Sensor in a Digital Microfluidic Platform," IEEE Sensors Journal, vol. 8, May 2008, pp. 628-635.

D. Brassard, L. Malic, F. Normandin, M. Tabrizian, and T. Veres, "Water-oil core-shell droplets for electrowetting-based digital microfluidic devices.," Lab on a chip, vol. 8, Aug. 2008, pp. 1342-1349.

R.S. Sista, A.E. Eckhardt, V. Srinivasan, M.G. Pollack, S. Palanki, and V.K. Pamula, "Heterogeneous immunoassays using magnetic beads on a digital microfluidic platform," Lab on a Chip, vol. 8, Dec. 2008, pp. 2188-2196.

R. Sista, Z. Hua, P. Thwar, A Sudarsan, V. Srinivasan, A Eckhardt, M. Pollack, and V. Pamula, "Development of a digital microfluidic platform for point of care testing.," Lab on a chip, vol. 8, Dec. 2008, pp. 2091-2104.

R. Mariella, "Sample preparation: the weak link in microfluidics-based biodetection.," Biomedical Microdevices, vol. 10, Dec. 2008, pp. 777-784.

* cited by examiner

Initial rate determination for glucose

HYDROGEN PEROXIDE DROPLET-BASED ASSAYS

1 RELATED APPLICATIONS

In addition to the patent applications cited herein, each of which is incorporated herein by reference, this patent application is related to and claims priority to U.S. Provisional Patent Application No. 60/892,971, filed on Mar. 5, 2007, entitled "Hydrogen Peroxide Droplet-Based Assays" and U.S. Provisional Patent Application No. 60/980,186, filed on Oct. 16, 2007, entitled "Hydrogen Peroxide Droplet-Based Assays," the entire disclosures of which are incorporated herein by reference.

2 GRANT INFORMATION

This invention was made with government support under DK066956-02 and GM072155-02 awarded by the National Institutes of Health of the United States. The United States Government has certain rights in the invention.

3 FIELD OF THE INVENTION

The present invention generally relates to the field of improved hydrogen peroxide assays.

In particular, the present invention is directed to hydrogen peroxide droplet-based assays, as well as droplet actuators for conducting such assays.

4 BACKGROUND OF THE INVENTION

A variety of assays make use of hydrogen peroxide as an intermediate for indirect analysis for a target molecule. For example, glucose may be measured by using glucose oxidase to produce hydrogen peroxide and using the hydrogen peroxide with a peroxidase to oxidize a substrate and produce a detectable signal, such as a color change. Examples of such oxidizable substrates include Amplex Red (Invitrogen) and PS-ATTO (Lumigen). There is a need in the art for approaches to miniaturizing and/or accelerating hydrogen peroxide assays.

Droplet actuators are used to conduct a wide variety of droplet operations. A droplet actuator typically includes a substrate associated with electrodes arranged to conduct droplet operations on a droplet operations surface of the substrate. Droplet actuators may also have top plates, which are generally separated in a parallel fashion from the droplet operations surface, forming a gap in which the droplet operations may occur. The gap may be filled with a filler fluid that is immiscible with the fluid that is to be manipulated on the droplet actuator. There's a need for expanding the capabilities of droplet actuators to include hydrogen peroxide based assays.

5 BRIEF DESCRIPTION OF THE INVENTION

The invention provides improved hydrogen peroxide assays, as well as droplet actuators for conducting such assays. The droplet actuators of the invention may be used to conduct droplet-based hydrogen peroxide assays.

In one embodiment, a method of conducting a hydrogen peroxide assay for detecting an analyte is provided. The method comprises combining hydrogen peroxide assay reagents and sample into a droplet having a volume which ranges from about 1 nL to about 10 µL and conducting the assay in the droplet to yield a detectable signal.

In another embodiment, a method of conducting a hydrogen peroxide assay is provided, wherein the method comprises combining hydrogen peroxide assay reagents and sample into a droplet and conducting the assay in the droplet to yield a detectable signal, wherein the assay produces a substantially linear result.

In yet another embodiment, another method of conducting a hydrogen peroxide assay for detecting an analyte is provided. The method comprises combining hydrogen peroxide assay reagents and sample into a droplet and conducting the assay in the droplet to yield a detectable signal, wherein substantially all of the analyte is consumed; detecting the signal; and analyzing the signal to determine the quantity of analyte in the sample.

In a further embodiment, a method of detecting multiple analytes on a single droplet actuator using a single detector is provided. The method comprises providing a droplet actuator device comprising a substrate comprising electrodes arranged for conducting droplet operations on a droplet operations surface of the substrate and one or more reservoirs in fluid communication with the droplet operations surface comprising one or more reagents for conducting an assay in which hydrogen peroxide is an intermediate.

The method further comprises using droplet operations to combine multiple sample droplets with multiple reagents to conduct multiple hydrogen peroxide assays on a single droplet actuator.

6 DEFINITIONS

As used herein, the following terms have the meanings indicated.

"Activate" with reference to one or more electrodes means effecting a change in the electrical state of the one or more electrodes which results in a droplet operation.

"Droplet" means a volume of liquid on a droplet actuator which is at least partially bounded by filler fluid. For example, a droplet may be completely surrounded by filler fluid or may be bounded by filler fluid and one or more surfaces of the droplet actuator. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to size of the resulting droplets (i.e., the size of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be mediated by electrodes and/or electric fields, using a variety of techniques, such as, electrowetting and/or dielectrophoresis.

The terms "top" and "bottom" are used throughout the description with reference to the top and bottom substrates of the droplet actuator for convenience only, since the droplet actuator is functional regardless of its position in space.

When a given component such as a layer, region or substrate is referred to herein as being disposed or formed "on" another component, that given component can be directly on the other component or, alternatively, intervening components (for example, one or more coatings, layers, interlayers, electrodes or contacts) can also be present. It will be further understood that the terms "disposed on" and "formed on" are used interchangeably to describe how a given component is positioned or situated in relation to another component. Hence, the terms "disposed on" and "formed on" are not intended to introduce any limitations relating to particular methods of material transport, deposition, or fabrication.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct droplet operations on the droplet, the droplet is arranged on the droplet actuator in a manner which facilitates sensing of a property of or a signal from the droplet, and/or the droplet has been subjected to a droplet operation on the droplet actuator.

7 BRIEF DESCRIPTION OF THE DRAWINGS

8 DETAILED DESCRIPTION OF THE INVENTION

The present invention relates to providing improved hydrogen peroxide assays, as well as droplet actuators for conducting such assays. The droplet actuators of the invention may be used to conduct droplet-based hydrogen peroxide assays. They may also be associated with detectors for analyzing the results of the hydrogen peroxide assays of the invention. They may be provided as components of systems which control droplet operations and/or detection for conducting the hydrogen peroxide assays. Measurement by the detector may be used to quantify the presence of an analyte in a sample.

8.1.1 Hydrogen Peroxide Assay

In general, an oxidase in the presence of an oxidizable analyte is used to generate hydrogen peroxide. In the presence of a peroxidase and the hydrogen peroxide, a substrate may be converted into a signal molecule. The signal molecule may produce or be used to produce a measurable signal, such as a color change, chemiluminescence or fluorescence. The invention provides a droplet-based hydrogen peroxide assay in which a sample droplet including an oxidizable analyte is combined using droplet operations with one or more droplets comprising an oxidase, a peroxidase, and a substrate that can be used to produce a signal molecule in the presence of peroxide and peroxidase. For example, a droplet comprising an oxidizable analyte may be transported using one or more droplet operations into contact with one or more droplets comprising the oxidase, the peroxidase, and/or the substrate. The oxidase may be selected to be specific to the oxidizable analyte, e.g., glucose oxidase for glucose. The peroxidase may be selected to be specific to the substrate, e.g., be horseradish peroxidase.

Figure 1:
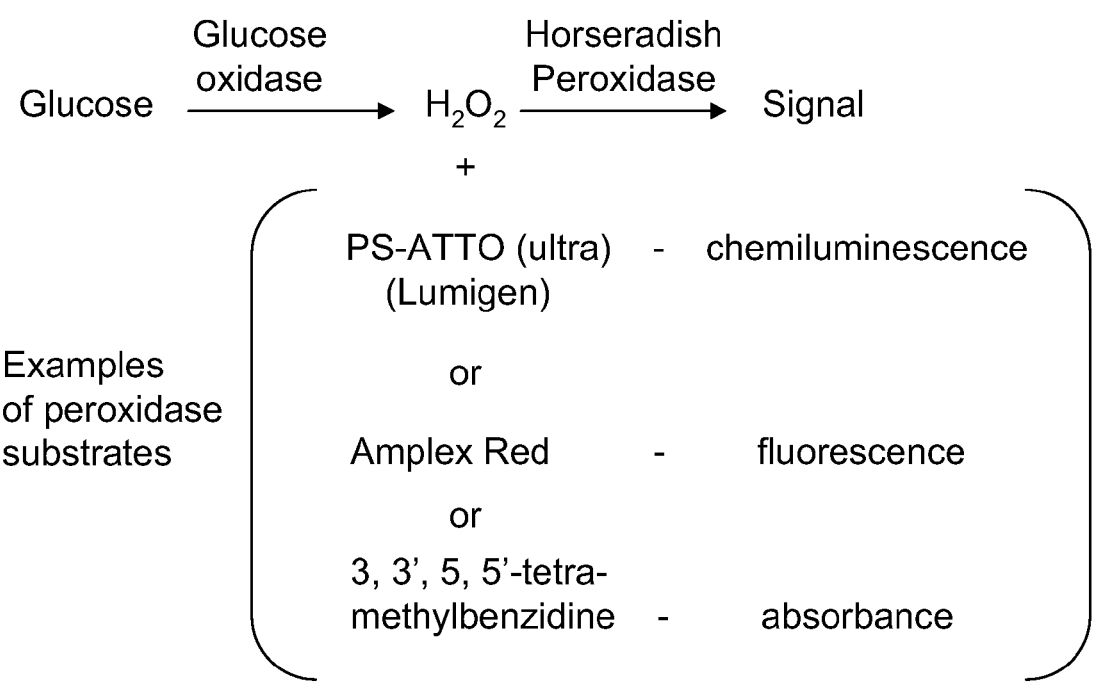
FIG. 1 illustrates various aspects of providing a hydrogen peroxide based glucose assay in accordance with one embodiment of the present invention.

As an example, the invention can provide a hydrogen peroxide based glucose assay, FIG. 1 illustrating various aspects of the assay. In general, a sample including glucose is combined with glucose oxidase in the presence of an amount of a peroxidase, such as horseradish peroxidase, and a signal molecule to produce a detectable signal. Examples of other suitable analytes susceptible to detection using the hydrogen peroxide assays of the invention include creatinin, lactate, pyruvate, bilirubin, glutamate, and other metabolites present in blood.

Any substrate which produces a signal molecule in the presence of hydrogen peroxide under appropriate enzymatic conditions may be used in the assays of the invention. Examples include PS-ATTO (ultra) from Lumigen and Amplex Red from Invitrogen. Signal molecules may be selected to permit detection in microliter or smaller droplets, e.g., by absorbance, chemiluminescence and/or fluorescence.

8.1.2 Microscale Hydrogen Peroxide Assay

In one embodiment, the invention provides a microscale hydrogen peroxide assay. In this embodiment, a sample is combined with the hydrogen peroxide assay reagents in a microdroplet. The reaction produces a signal, which is detected. The signal is used to determine the amount of the target analyte present in the sample. The hydrogen peroxide assay reagents may, for example, include oxidase, an excess of peroxidase, and a substrate which can be converted in the presence of hydrogen peroxide and peroxidase into a signal molecule. The reagents may also include any additional reagents or cofactors suitable for enhancing the reaction.

In one embodiment, the reaction takes place in a droplet partially or completely surrounded by an oil, such as a silicon oil. In another embodiment, the reaction takes place on a droplet actuator surface. The reagents may be combined on the droplet actuator surface using droplet operations. The droplet actuator may also include a top plate separated from the surface to form a gap in which the droplet is arranged. Detection of the signal may take place while the droplet is on the droplet actuator. Further, droplet operations may be used to combine one or more droplets including one or more of the hydrogen peroxide reagents with the sample in the presence of the detector, so that a maximum amount of signal may be captured.

In one embodiment, the hydrogen peroxide assays of the invention may be performed using exceedingly small sample volumes. In one embodiment, the sample volumes range from about 1 nL to about 10 µL, or from about 10 nL to about 1 µL, or less than about 500, 400, 300, 200, 100 nL. Reaction volumes may be similarly small. For example, in one embodiment, the reaction volume including the sample and all hydrogen peroxide reagents ranges from about 1 nL to about 10 µL, or from about 10 nL to about 1 µL, or less than about 500, 400, 300, 200, 100 nL.

Other advantages include reduced time to results due to faster kinetics in the miniaturized format for the assays and higher throughput due to multiplexing. For example, in one embodiment, the system executes hydrogen peroxide assays in less than about 5, 4, 3, 2 or 1 minutes or less than about 45 or 30 seconds.

8.1.3 Hydrogen Peroxide Assay with Substantially Linear Kinetics

Figure 2:
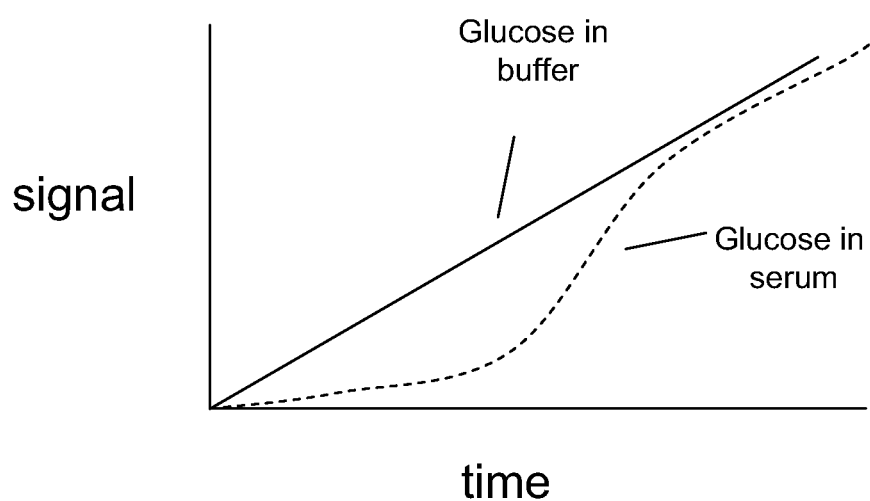
FIG. 2 illustrates a velocity sketch showing the rate of signal production in a sample as compared to signal production in buffer.

FIG. 2 illustrates a velocity sketch showing the rate of signal production in the sample as compared to signal production in buffer. Glucose, glucose oxidase, hydrogen peroxidase, and a chemiluminescent or fluorescent acceptor were utilized. The assay conditions were designed to evaluate the initial rate of signal production. All the glucose in the sample was not consumed, and the reaction kinetics was at an initial linear rate velocity. The solid line represents the reaction in buffer. Because there are no inhibitors, straight line kinetics proportional to the amount of glucose in the sample was observed. The dotted line represents the reaction in serum. A lag in the initial rate was observed, presumably due to the presence of inhibitors in the serum. In this sample, the kinetics do become linear, but only after the initial lag. The lag may be 1-5 minutes, for example. For the desired applications of quantifying the amount of analyte (glucose) in a sample within seconds, these assay conditions are not desirable.

The inventors have surprisingly discovered that the initial lag can be overcome in the presence of inhibitors by providing an excess amount of peroxidase, e.g. horseradish peroxidase. In this manner, the impact of the endogenous inhibitors may be reduced or eliminated. By increasing the peroxidase concentration, and leaving the glucose oxidase concentration fixed, the inventors observed linear kinetics in serum. The lag was minimized to the point of being inconsequential. In one embodiment, the process employs HRP in a range from about 1 ug/ml to about 100 µg/ml. In this embodiment, glucose oxidase may be employed in typical amounts, e.g., about 200 µg/ml.

When conducting peroxide based assays on biological fluids, such as blood, serum, and plasma, molecules may be present in the biological fluid which interfere with the linearity of the assay results. For example, various inhibitors or components that may compete with or consume a reaction component or intermediate may be present in the biological fluids. Examples include hemoglobin, ascorbate (vitamin C), bilirubin, glutathione, and catalase. The invention provides a method for producing a linear signal which reliably indicates the amount of analyte in the sample, even in the presence of such interfering substances. For example, the invention provides a method of conducting a hydrogen peroxide assay to determine the quantity of an analyte in the biological fluid in the presence of inhibiting substances, which method produces a generally or substantially linear result. The substantially linear result may be produced by combining a sample including the analyte with an oxidase, an excess of peroxidase, and an oxidizable signal molecule, such as Amplex Red.

The peroxidase may be provided in an excess amount which is sufficient to result in a generally or substantially linear result.

8.1.4 Flash Hydrogen Peroxide Assays

Figure 3:
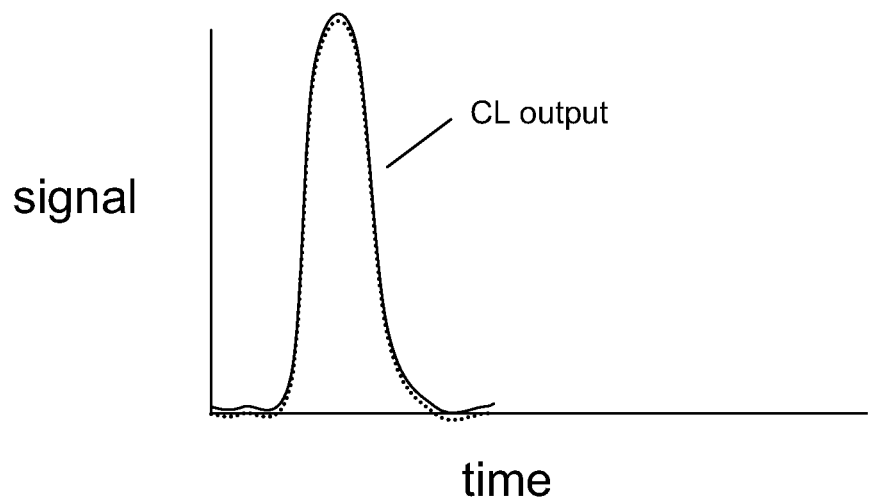
FIG. 3 illustrates an end-point assay for measuring the amount of analyte (glucose) in a sample.

FIG. 3 illustrates an end-point (also termed 'flash') assay for measuring the amount of analyte (glucose) in the sample. In the end-point assay, all of the analyte was consumed, and the signal represents substantially the entire amount of analyte contained in the sample. The reaction kinetics in the end-point assay are increased by elevating both the oxidase and the peroxidase. The reaction was complete in approximately 1-2 minutes. The impact of the endogenous inhibitors in the serum is minimal because the ratio of analyte, e.g. glucose, to inhibitors in serum is so high that the effect of the inhibitor becomes minimal and negligible in the total signal output. The measurement of the end point assay can be carried out in the droplet actuator, directly under the sensor, thus maximizing the capture of signal output. Serum and reagents may be combined using droplet operations, and capture of signal can begin immediately. In one embodiment, the process employs peroxidase (e.g., horseradish peroxidase) in a range from about 1 ug/ml to about 100 ug/ml, and oxidase (e.g., glucose oxidase) in an amount exceeding about 200, 300, 400, 500, 600, 700, 800, 900 ug/ml, or exceeding about 1 mg/ml.

8.1.5 Multiplexed Hydrogen Peroxide Assays

Use of the common intermediate hydrogen peroxide provides for analysis of multiple analytes using one common intermediate, and one detector scheme. Thus, the invention provides a droplet actuator comprising reagents for analyzing multiple analytes susceptible to analysis using a hydrogen peroxide assay. In one embodiment, multiple reagent droplets and sample droplets are provided on the droplet actuator combined using droplet operations to conduct multiple hydrogen peroxide assays. The assays may be conducted in a substantially parallel manner or sequentially. In one embodiment, the assays are conducted sequentially so that each assay may be conducted in the presence of a single detector. Following detection, and as a droplet may be transported using droplet operations away from the detector, the subsequent assay may be set up in the presence of the detector using droplet operations. Alternatively, assays may be set up away from the detector, and transported into the presence of the detector. The droplet actuator and/or detection device may be electronically coupled to and controlled by a processor. The processor may, for example, be programmed to control the droplet operations electrodes in order to affect the droplet-based hydrogen peroxide assay protocol. In one embodiment, where the curve is initially not linear, multiple reactions can be started in sequence and incubated until the curve becomes linear, at which point they can sequentially be transported using droplet operations into the presence of the detector.

8.2 Droplet Actuator

For examples of droplet actuator architectures suitable for use with the present invention, see U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000, both to Shenderov et al.; and Pollack et al., International Patent Application No. PCT/US 06/47486, entitled "Droplet-Based Biochemistry," filed on Dec. 11, 2006, the disclosures of which are incorporated herein by reference.

8.3 Fluids

For examples of sample fluids useful according to the approach of the invention, see the patents listed in section 8.2, especially International Patent Application No. PCT/US 06/47486, entitled "Droplet-Based Biochemistry," filed on Dec. 11, 2006. In some embodiments, the fluid includes a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, fluidized tissues, fluidized organisms, biological swabs and biological washes.

8.4 Filler Fluids

The droplets used in the assays of the invention may be completely or partially surrounded by a filler fluid. The filler fluid may, for example, be a low-viscosity oil, such as silicone oil. Other examples of filler fluids are provided in International Patent Application No. PCT/US 06/47486, entitled "Droplet-Based Biochemistry," filed on Dec. 11, 2006.

9 CONCLUDING REMARKS

The foregoing detailed description of embodiments refers to the accompanying drawings, which illustrate specific embodiments of the invention. Other embodiments having different structures and operations do not depart from the scope of the present invention.

This specification is divided into sections for the convenience of the reader only. Headings should not be construed as limiting of the scope of the invention.

It will be understood that various details of the present invention may be changed without departing from the scope of the present invention. Furthermore, the foregoing description is for the purpose of illustration only, and not for the purpose of limitation, as the present invention is defined by the claims as set forth hereinafter.

We claim:

1. A method of conducting a hydrogen peroxide assay for detecting an analyte, the method comprising:
    (a) combining hydrogen peroxide assay reagents and a sample into a droplet and conducting the assay in the droplet surrounded by oil in a droplet actuator to yield a detectable signal, the hydrogen peroxide reagents comprising an oxidase, a peroxidase, and a substrate which produces a signal molecule in the presence of a peroxidase and hydrogen peroxide, and the peroxidase provided in an amount effective to produce a substantially linear response, wherein the assay comprises a flash assay in which substantially all of the analyte is consumed, and wherein the sample and reagents for conducting the flash assay are surrounded by oil and are combined to form the droplet in the presence of a sensor sensing the signal, and wherein the combining is accomplished on a droplet actuator using electrowetting-mediated droplet operations; and
    (b) analyzing results of the assay based on measurement by the sensor.

2. The method of claim 1 wherein the peroxidase comprises horseradish peroxidase.

3. The method of claim 1 wherein the analyte comprises glucose and the oxidase comprises glucose oxidase.

4. The method of claim 1 wherein the sample comprises a biological fluid.

5. The method of claim 4 wherein the result has a lag time which is less than about five seconds.

6. The method of claim 4 wherein the result has substantially no lag time.

7. The method of claim 1 wherein the droplet has a size which ranges from about 10 nL to about 1 µL.

8. The method of claim 1 wherein the droplet has a size which ranges from about 1 nL to about 500 nL.

9. The method of claim 1 wherein the analyte is selected from a group consisting of metabolites present in the blood susceptible to production of hydrogen peroxide in the presence of an oxidase.

10. The method of claim 1 wherein the analyte is selected from a group consisting of creatinin, lactate, pyruvate, bilirubin, glutamate.

11. The method of claim 1 wherein the oil comprises a silicon oil.

12. The method of claim 1 wherein the amount of peroxidase is in a range of about 1 µg/ml to about 100 µg/ml.

13. The method of claim 1 wherein the sample comprises serum and the peroxidase is in an amount sufficient to produce substantially linear kinetics.

14. The method of claim 1 wherein the sample comprises one or more inhibitors and the peroxidase is in an amount sufficient to produce a substantially linear response.

15. A method of conducting a hydrogen peroxide assay, the method comprising:
    (a) combining in the presence of a sensor hydrogen peroxide assay reagents and a sample into a droplet and conducting the assay in the droplet surrounded by oil in a droplet actuator to yield a detectable signal, and wherein the reagents are selected to cause the assay to produce a substantially linear result, and wherein the sensor is sensing the signal upon the combining of the hydrogen peroxide assay reagents and a sample; and
    (b) analyzing results of the assay based on measurement by the sensor.

16. The method of claim 15 wherein the amount of peroxidase is in a range of about 1 µg/ml to about 100 µg/ml.

17. The method of claim 15 wherein the peroxidase is provided in an amount sufficient to result in a substantially linear response.

18. The method of claim 15 wherein the sample comprises serum and the peroxidase is in an amount sufficient to produce substantially linear kinetics.

19. The method of claim 15 wherein the peroxidase comprises horseradish peroxidase.

20. The method of claim 15 wherein the sample comprises one or more inhibitors and the peroxidase is in an amount sufficient to produce a substantially linear response.

21. A method of conducting a hydrogen peroxide assay for detecting an analyte, the method comprising:
    (a) combining in the presence of a sensor hydrogen peroxide assay reagents and sample into a droplet and conducting the assay in the droplet surrounded by oil in a droplet actuator to yield a signal detectable by the sensor, wherein substantially all of the analyte is consumed in less than about 5 minutes, and wherein the sensor is sensing the signal upon the combining of the hydrogen peroxide assay reagents and sample;
    (b) detecting the signal; and
    (c) analyzing the signal to determine the quantity of analyte in the sample.

22. The method of claim 21 wherein substantially all of the analyte is consumed in less than about 2 minutes.

23. The method of claim 21 wherein the sample comprises a biological sample.

24. The method of claim 21 wherein the sample is selected from the group consisting of blood, serum, and plasma.

25. The method of claim 21 wherein the amount of peroxidase is in a range of about 1 µg/ml to about 100 µg/ml.

26. The method of claim 21 wherein the peroxidase is provided in an amount sufficient to result in a substantially linear result.

27. The method of claim 21 wherein the sample comprises serum and the peroxidase is in an amount sufficient to produce substantially linear kinetics.

28. The method of claim 21 wherein the peroxidase comprises horseradish peroxidase.

29. The method of claim 21 wherein substantially all of the analyte is consumed in less than about 4 minutes.

30. The method of claim 21 wherein substantially all of the analyte is consumed in less than about 3 minutes.

31. The method of claim 21 wherein substantially all of the analyte is consumed in less than about 1 minute.

32. The method of claim 21 wherein the sample comprises one or more inhibitors and the peroxidase is in an amount sufficient to produce a substantially linear response.

\* \* \* \* \*